(12) United States Patent
Stilp

(10) Patent No.: US 6,981,569 B2
(45) Date of Patent: Jan. 3, 2006

(54) EAR CLIP

(76) Inventor: Paul J. Stilp, 2903 Propst Dr., Aliquippa, PA (US) 15001-1132

( * ) Notice: Subject to any disclaimer, the term of this patent is extended or adjusted under 35 U.S.C. 154(b) by 148 days.

(21) Appl. No.: 10/420,172

(22) Filed: Apr. 22, 2003

(65) Prior Publication Data
US 2004/0188173 A1 Sep. 30, 2004

(51) Int. Cl.
*H04R 25/00* (2006.01)
(52) U.S. Cl. .................................................. 181/129
(58) Field of Classification Search ............... 181/129, 181/128, 130–137
See application file for complete search history.

(56) References Cited

U.S. PATENT DOCUMENTS

| | | | |
|---|---|---|---|
| 3,807,526 A * | 4/1974 | Sygnator | ..................... 181/175 |
| 4,187,838 A | 2/1980 | Dubrowski | |
| 4,231,360 A | 11/1980 | Zloczysti et al. | |
| 5,835,609 A * | 11/1998 | LeGette et al. | .............. 381/385 |
| 6,056,082 A | 5/2000 | Lindgren et al. | |
| D437,048 S | 1/2001 | Hirshfeld | |
| 6,302,111 B1 | 10/2001 | Bremenstul | |
| D452,909 S | 1/2002 | Saulce | |
| 6,427,800 B1 | 8/2002 | Hiselius et al. | |
| 6,442,279 B1 | 8/2002 | Preves et al. | |
| 6,445,805 B1 * | 9/2002 | Grugel | ....................... 381/330 |
| D468,419 S | 1/2003 | Vesterlund | |

FOREIGN PATENT DOCUMENTS

| | | |
|---|---|---|
| EP | 1 222 945 A1 | 7/2002 |
| GB | 2 375 967 A | 12/2002 |

* cited by examiner

*Primary Examiner*—Kimberly Lockett
(74) *Attorney, Agent, or Firm*—Christine W. Trebilcock; Alicia M. Passerin; Cohen & Grigsby, P.C.

(57) ABSTRACT

A hearing protection device and method of natural sealing provides an ear clip designed with two elongated elements. The elements each have a flexible part or cushions at one end and are attached with a tension mechanism that applies pressure forcing the ends together. The flexible part or cushion ends contact the wearer, one behind the lower ear and the other at the auricle skin flap pressing the flap to cover the ear canal.

17 Claims, 3 Drawing Sheets

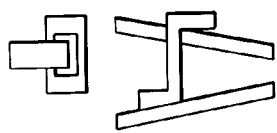
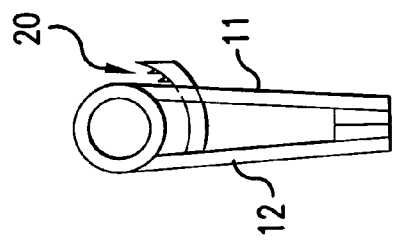
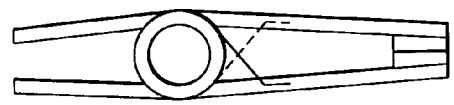
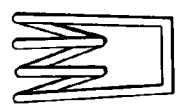
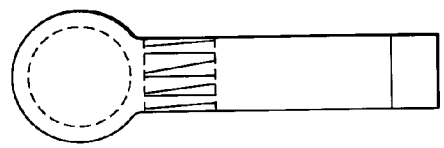
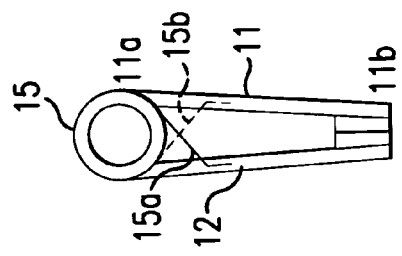
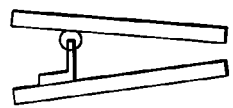
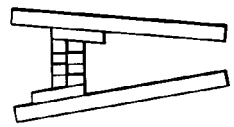
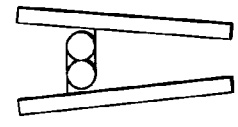
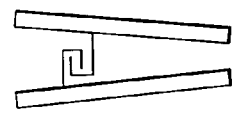
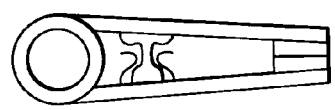

EAR CLIP

FIELD OF THE INVENTION

This invention relates to a hearing protection device and, more particularly, to an ear clip and natural sealing concept.

BACKGROUND OF THE INVENTION

In today's society we are exposed to an increasing level of noise. Hearing devices are mandated in many industrial and manufacturing environments to protect against such noise. Other perhaps less obvious activities have also increased our exposure to potentially dangerous levels of noise, including hair blow-dryers, power mowers or other power equipment, airplanes, etc. In addition to noise concerns, some individual's ears are sensitive to water or contaminants, such as from a shower or swimming. All such tasks prove to be a challenge and show a genuine need for a safer natural ear and hearing protection.

Common solutions for attenuating excessive levels of noise include passive aural hearing protectors such as padded cup-like structures known as "Mickey Mouse Ears" or ear muffs, and ear plugs. Ear plugs are inserted into the ear sometimes requiring adjustment for proper functioning. If the adjustment is ineffective, the wear's safety may be compromised. Ear muffs cover the ears to filter out excessive noise passively. Ear muffs require less adjustment than plugs, but may be cumbersome or uncomfortable.

It is desirable to have a method and solution for hearing protection that does not compromise the wearer's safety and/or well-being and is convenient to use. Many times safety may be inadvertently compromised without thought or concern of an individual resulting in mishap and damage which could have been avoided.

Accordingly, it is an object in an embodiment of the present invention to provide a form of hearing protection that will not damage the wearer's hearing canal caused by adjustment of "in the ear canal" plugged activity. In an embodiment it is an object to minimize the risk for hearing protection damage of devices due to improper adjustment and/or poor design whereby constant noise level activity is causing continual damage due to high/low attenuation levels causing irreparable damage. In another example, the device covers the ear canal with the auricle flap to minimize or prevent water from accessing the canal. Further, in an embodiment of the invention it is an object to provide a more natural self sealing approach via the auricle flap to decrease possible hearing damage for loud or excessive noise.

SUMMARY OF THE INVENTION

Generally, the present invention provides a passive aural noise or hearing protector device and method for natural sealing concept. There are periods when noise levels are high and also periods where the levels are low or at an normal ambient level. The hearing protector device is designed to affix about a user's ear to provide sufficient pressure to the auricle flap so that it covers the ear canal to filter out or block exposure to noise. It is for any duration of wear or for wear during exposure to long periods of noise levels, such as over an eight hour period. An embodiment is anticipated to filter noise levels above that recommended by the Occupation Health Safety Association which sets a standard noise level limit exposure of 90 dBA. In an example, the invention minimizes or prevents water from accessing the ear canal.

An embodiment of the device comprises a first and second elongated leg or element each having a first end and a second end, and an inner side. A tension mechanism or tensioner connects to the ends of both elements or an area of the inner side of each element to moveably attach the elements. In an embodiment, the tensioner affixes to at least a part of an area of each inner side that is located closer to the first end than the second end of each element. In another embodiment, the tensioner affixes to an area of each inner side located about equidistant between the first and second end of each element. The area is selected in conjunction with the type of tensioner employed so that the elements open and close relative to each other. Tensioner is sufficiently tensioned so that elements force toward each other or have a grasp. For example, tensioner is a hinge, breakover snap, spring, coil, spring loaded lock; or an elastic bow or bent article; or cushioning article or material of some resilience. In an example, the tension mechanism comprises a pivot upon design compression of the first and second elements creating an inward collapse of the second ends towards each other. In another example, two rivets fasten to auricle leg end which has two female holes on each side of rivets. Both accept the opposite element via outboard metal design that protrudes through the holes of the element completing the fastening connections at each which is mounted parallel with leg (tang). Alternatively, one or both of the first ends connect with tensioner to provide a combination or a single unit.

When the clip elements are in an open position the tension mechanism adjusts the first ends of the elements towards each other opening the second ends apart. It applies minimal yet sufficient pressure to allow auricle skin flap to close the canal opening.

In an embodiment, the second ends of both elements contain a more flexible part or are comprised of a resilient material, such as plastic or a flexible metal for contacting the wearer. In another embodiment, a pad, cushion or the like is attached to the second ends or inner side of each element. The flexible part or cushion ends of the elements contact the wearer, one behind the lower ear and the other at the auricle skin flap gently pressing the flap to cover the ear canal. The contact pad on one element contacts the auricle or auricle skin near to or at the entrance of the wearer's ear canal and the contact pad of the other element contacts the area near to or at the cavity of the neck and ear intersection.

The pads are made of any flexible or elastic material such as, for example, rubber, foam, fabric, gel, and are attached to the second ends with adhesive, stitching, stapling, hook and latch, or other attachment means. In an example, contact pad are pressed through a hole at the end of each element so that the attachment is sufficiently secure and stabile, yet cushion pads remain flexible for a user's comfort. In another example, contact pads flexibly attach to the elements to allow for some give or swivel for enhanced comfort of the wearer. In another example, the more flexible part contacts the wearer and pads are not used. The device is worn so that auricle skin flap folds forming a natural essentially air, water-tight seal of the ear canal. In design, contact pads and tension mechanism are selected to provide flexibility and comfort. Clip elements, pads, and locking feature are designed in a variety of lengths, widths, heights and depth which are selected advantageously to fit dimensions of desired embodiment.

An embodiment of the present invention provides a means and method of utilizing the auricle flap natural sealing process. Clip elements are separated or opened relative to each other to slip over and around the wearer's ear. Once around, the elements are allowed to close having the auricle ear side covering the ear channel while the neck side is placed under the ear providing tension to keep the auricle flap closed. One clip is used with each ear. By design it can adjust to fit any number of people. In another example, the invention is used with animals exposed to noise environments.

The invention provides a self motivating solution and a better means for safety as applied to hearing protection by offering a device that covers the opening of the exposed inner ear canal more safely and without penetrating the ear with foreign objects such as: plugs, foam, etc. and the like. Such objects possibly cause hearing injury rather than protection. Wax may be pushed downstream further into the canal. Prior art designs to protect a human's hearing can also be flawed by lack of instruction or improper fit to attain optimum fit for protecting hearing. In an example this natural sealing process overcomes these shortcomings by utilizing the ear's own seal.

Other features, aspects and advantages of the present invention will become better understood or apparent from the following detailed description, drawings and appended claims of the invention.

BRIEF DESCRIPTION OF THE DRAWINGS

FIG. 2a shows a side view of another embodiment of the invention.

FIG. 2b shows a top view of an embodiment.

FIG. 2c shows an example of a tension mechanism used in an embodiment of the invention.

FIG. 3 shows a side view of another embodiment of the invention.

FIG. 4a shows a side view of another embodiment of the invention with interlocking features.

FIG. 4b shows another view of an embodiment of the invention with interlocking features.

FIGS. 5a–5e show various embodiments of a tension mechanism in examples of the invention.

DESCRIPTION OF EXAMPLES OF THE INVENTION

Figure 1A:
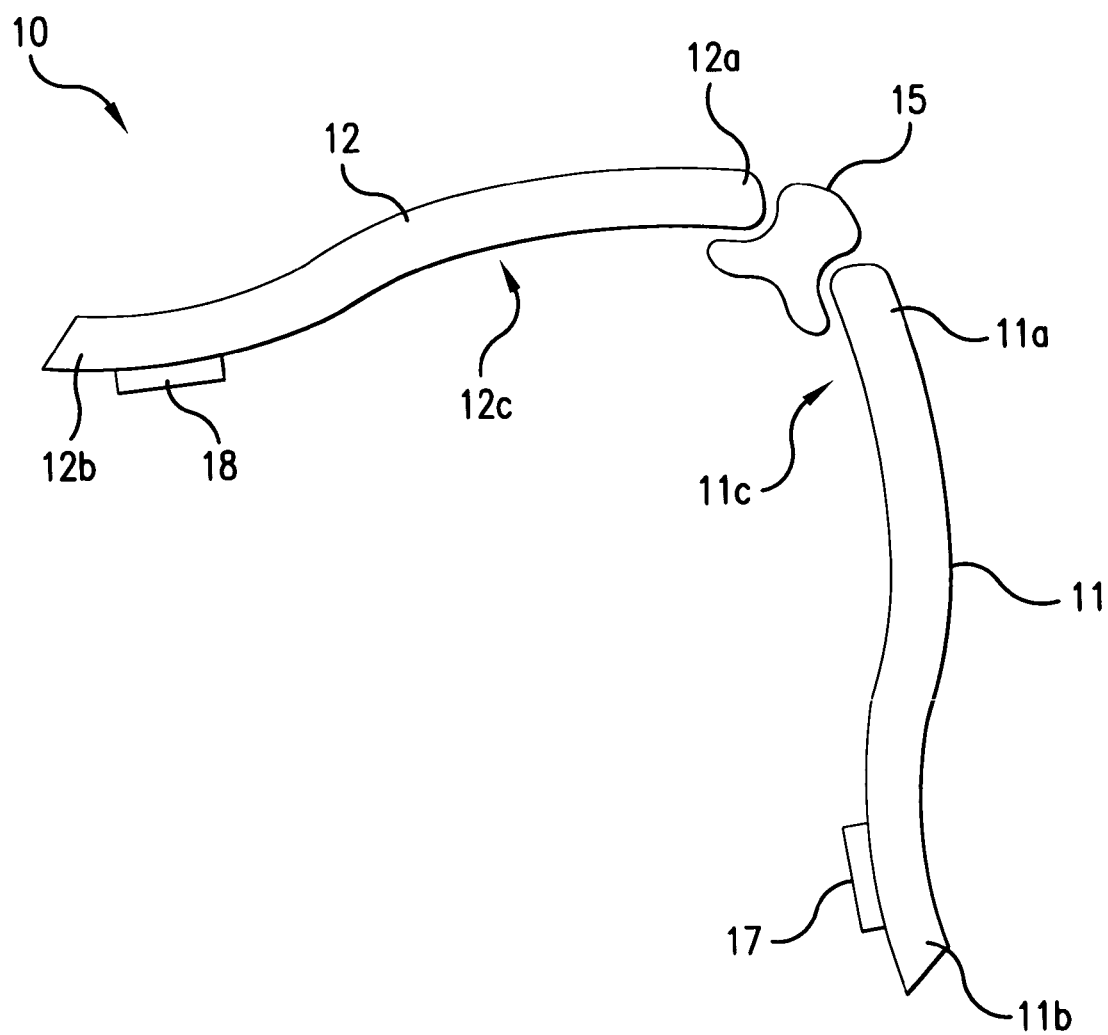
FIG. 1 is a side view of an embodiment of the present invention.
Figure 1B:
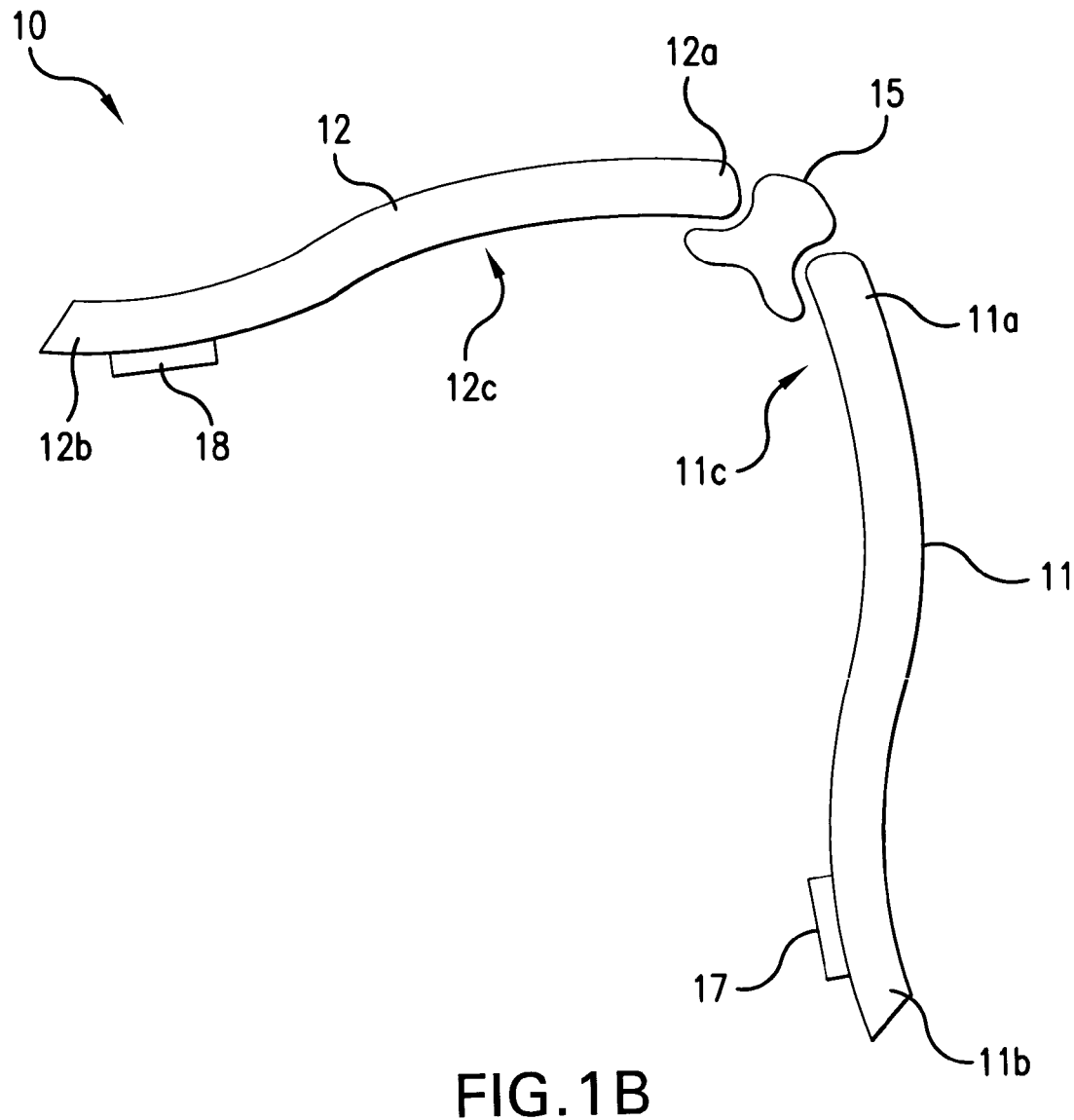

Referring now to FIG. 1, hearing protection device or ear clip 10 is shown having two clip elements 11 and 12 each with a first end, 11a and 12a; a second end, 11b and 12b; and inner sides, 11c and 12c. Tension mechanism 15 connects clip elements 11 and 12 together. In this example, it attaches to an area of inner sides 11c and 12c and at the second ends 11b and 12b to moveably attach first element 11 to second element 12. Cushion pads 17 and 18 are provided near second ends 11b and 12b. Pads 17 and 18 contact the wearer, one behind the lower ear and the other at the auricle skin flap gently pressing the flap to cover the ear canal. Tension mechanism 15 adjusts the elements relative to each other under tension so that pads 17 and 18, align and rest against a wearer's ear and ear-neck cavity, respectively. For instance, auricle pad 18 is designed to cover a wearer's auricle flap. Neck-ear lobe cavity pad 17 fits under the ear of the wearer, in an example, in the ear-neck lobe cavity. Pads are designed to both fit securely on the second ends and be flexible to comfort to the wearer.

Tensioner 15 can include a variety of mechanisms. For example, as shown in FIG. 2, tension mechanism 15 is a spring assembly. The top view shows the base as the spring(double circle) having two legs with offset pads at the ends. The spring is wound metal. Optionally, it is covered in rubber. The legs may also be covered in rubber. Wire ends 15a and 15b each protrude forward offsetting each other: wire leg end folding down forward from high to low then folding inward to attach to an inner area of a clip element while the other is opposite in nature but attaches to the other clip element. The clip is donned by separating the elements and element 11 to contact the auricle flap portion of the exterior ear while the other element contacts the ear-neck cavity aft and inboard of the ear lobe (exterior ear). In this example, element 11 is longer than element 12. The spring feature is designed to be out of the contact zone of the ear lobe just below so as to not cause harm to the wearer. It provides sufficient tension to compress the auricle flap due to the wind and offsetting leg wire of the spring whereby the wire/metal leg end tangs facing inboard toward each other provide the tension as positioned on the clip. Various dimensions for the elements, tensioner and pads, such as length, width, height, and depth, are employed depending on populace demand.

FIG. 2b shows a top view of another example of the invention in an alternative design setting. This example resembles the example above except a rounded base top leg is added so the wearer presses and releases the clip via the extension. Again there are various dimensions in length, width, height and depth for clip elements, pads, and locking feature depending on populace demand.

FIGS. 4a and 4b provide another example of an embodiment of the invention having a different clip design. This example provides an interlocking feature comprising an arm angled off at the ear-neck clip leg that protrudes through the leg for the auricle flap mating which has several "shark teeth" tangs 20 arranged as slots and cut-out of the arm. This acts as a consecutive flowing adjustable locking feature which locks and secures against the cutout metal of the auricle flap leg. The top view shows a new clip design with a base with optional wound metal completing 360 degrees and two appendages spun out forming the legs. Alternatively, without the complete overlapping metal 360 degree wound metal can be a 180 degree base forming two legs ending each with their own pad and function. In another example, an interlocking feature has an arm from the ear-neck leg protruding through the auricle flap leg. This interlocking feature spinning off of the legs with double continuous offsetting 90 degree angles is mounted as required. In an example, the metal is covered with rubber for protection and safety for wearer from the sharp metal end insuring convenience and safety in use. The legs move (such as in FIGS. 2 and 3) to flow away from circled base ending in two offsetting pads with individual functions for hearing protection. The tensioner feature gives tension, lock and release. It is designed to fit below the ear lobe for securing and releasing the clip element.

FIGS. 5a–5e show various embodiments of a tension mechanism in examples of the invention. An example, as provided in FIG. 5a, is similar to design of FIG. 4b but also offers leg pads that overlap about the center, one above the other designed as a closer fit for populace demand. In other examples of the invention the tensioner is designed to function with an overlapping leg configuration or straight leg configuration, wherein the legs are of same or different lengths. In an example, tensioner is a spring mounted with rivets, such as steel or other metal. In an example it features an onto the ear-neck leg that accepts upon locking/mating a teat base and head whereby the head presses into the cavity of the spring section completing the locking feature sufficient to secure a comfortable sealing effect. The teat base and head is constructed of solid material such as plastic or metal, including steel, aluminum, for example. The user operates the tensioner to don the clip element for performance.

Another example shown in FIG. 5b is designed with a double angled approximately 90 degree metaled tanged interlocking feature mounted to appropriate leg via an approximately 90 degree leg fastened with rivets. Donning and releasing is performed by a twist and act of the flexible spring effect of the metaled leg design of the clip. In FIG. 5c, another example provides a tensioner having two pieces, such as square elements or rolled circled balls of ferrous (iron), one of which is magnetized. The attraction of the magnet to the non magnetic ferrous ball acts as a lock feature completing the interlocking effect. Release is performed by the wearer as required. Another example, as in FIG. 5d, provides two zippered tanged toothed metal/plastic connect that interlock when squeezed together. Both are mounted to existing legs and fastened with rivets. The wearer operates the functions for donning and releasing the clip. In FIG. 5e, an example of the present invention uses a similar approximately 90 degree rivet mounted arm mounted off of the ear-neck leg with an additional approximately 90 degree arm from same arm that connects to a 360 degree mounted ring mounted onto the auricle flap leg thereby an interlocking effect takes place. The rivet and ring are metal or another durable material such as plastic. Donning and releasing functions are performed by wearer. As can be seen, there exist various ways and designs for preparing the clip element, pads and tensioner. Dimensions vary and are adjustable to complement the tensioner and other clip features including ultimate design elements and wearer's preferences. These examples demonstrate just a few possible ways of designing and constructing the inventive ear clip disclosed herein.

While the foregoing has been set forth in considerable detail, it is to be understood that the drawings and detailed embodiments are presented for elucidation and not limitation. Design variations, especially in matters of shape, size and arrangements of parts, may be made but are within the principles of the invention. Those skilled in the art will realize that such changes or modifications of the invention or combinations of elements, variations, equivalents or improvements therein are still within the scope of the invention as defined in the appended claims.

What is claimed is:

1. A hearing protection device comprising a first and second elongated element each said elements having an inner side and a first and second end, and a tension mechanism connecting said elongated elements together, said tension mechanism moveably attached to said inner side of each said first and second elements so that said second ends thereof are pressured toward each other and fit about one of a user's ears to cover the canal of said ear with the auricle skin flap.

2. A hearing protection device of claim 1 further including a pad flexibly attached on each said second end of said first and second elements.

3. A hearing protection device of claim 2 wherein one said pad contacts the wearer near the auricle and another pad contacts the wearer near the cavity of neck and ear intersection thereby pressing the auricle skin flap to cover the ear canal opening.

4. A hearing protection device of claim 1 wherein said tension mechanism comprises of one selected from the group comprising a hinge, breakover snap, spring, coil, elasticizer, bow, bent article, cushion material, and magnetic pieces.

5. A hearing protection device of claim 1 wherein said tension mechanism and one of the elements comprises a single unit.

6. A hearing protection device of claim 1 wherein said tension mechanism and both of the elements comprise a single unit.

7. A hearing protection device of claim 1 wherein said element second ends comprise flexible portions.

8. A hearing protection device of claim 2 wherein said pads are made of a flexible or elastic material.

9. A hearing protection device of claim 2 wherein said pads are selected from the group comprising of rubber, foam, fabric, and gel.

10. A hearing protection device of claim 2 wherein said pads are attached to said second ends with adhesive, stitching, stapling, hook and latch, or other attachment means.

11. A method of protecting hearing comprising separating the end of a first element away from the end of a second element being tensioned towards it, said first and second elongated elements being moveably attached to one another at one of their ends and being tensioned toward each, and donning elements about an ear so that the free end of one element presses the auricle flap over the ear canal and the free end of the second element rests below or behind the ear.

12. A hearing protection device comprising a first and second elongated element each said element having an inner side and a first and second end, a tension mechanism moveably attached to said inner side of each of said first and second elements so that said second ends thereof are pressured toward each other and fit about a user's ear to cover the ear canal with the auricle skin flap, there being a pad flexibly attached on each said second end of said first and second elements, wherein one said pad contacts the wearer near the auricle and another pad contacts the wearer near the cavity of neck and ear intersection thereby pressing the auricle skin flap to cover the ear canal opening.

13. A hearing protection device of claim 1 wherein said tension mechanism is attached to said inner side of each element near said first ends of said elements.

14. A hearing protection device of claim 1 wherein said tension mechanism is attached to said inner side of each element at a point about equidistant between said first and second ends of each of said elements.

15. A hearing protection device of claim 1 wherein said tension mechanism comprises a base having a first and a second leg, said first leg folding to attach to said inner side of said second element and said second leg folding to attach to said inner side of said first element.

16. A hearing protection device of claim 1 wherein said tension mechanism further comprises an adjustable locking mechanism.

17. A hearing protection device of claim 15 wherein said adjustable locking mechanism comprises an arm having a plurality of teeth, said arm protruding from said first element and through said second element.

* * * * *